US00PP30975P2

(12) United States Plant Patent
Knosher

(10) Patent No.: US PP30,975 P2
(45) Date of Patent: Oct. 22, 2019

(54) ***COREOPSIS* PLANT NAMED 'ELECTRIC SUNSHINE'**

(50) Latin Name: ***Coreopsis* hybrid**
Varietal Denomination: Electric Sunshine

(71) Applicant: Ball Horticultural Company, West Chicago, IL (US)

(72) Inventor: Lynne Knosher, St. Charles, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/999,976

(22) Filed: Sep. 6, 2018

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
See application file for complete search history.

*Primary Examiner* — Anne Marie Grunberg
(74) *Attorney, Agent, or Firm* — Audrey Charles

(57) ABSTRACT

A new and distinct cultivar of *Coreopsis* plant named 'Electric Sunshine', characterized by its single-type, medium yellow-colored inflorescences having a burgundy-red colored eye zone, medium green-colored foliage, and vigorous, mounded growth habit, is disclosed.

1 Drawing Sheet

Latin name of genus and species of plant claimed: *Coreopsis* hybrid.
Variety denomination: 'Electric Sunshine'.

BACKGROUND OF THE INVENTION

The present invention relates to a new and distinct cultivar of *Coreopsis* plant botanically known as *Coreopsis* hybrid and hereinafter referred to by the cultivar name 'Electric Sunshine'.

The new cultivar originated in a controlled breeding program in Elburn, Ill. during November 2012. The objective of the breeding program was the development of *Coreopsis* cultivars having substantially continuous blooming throughout the summer, high vigor, and mounded growth habits.

The new *Coreopsis* cultivar is the result of cross-pollination. The female (seed) parent of the new cultivar is the proprietary *Coreopsis rosea* breeding selection coded C025-1, not patented, characterized by its single-type, white-colored inflorescences having a burgundy-colored eye zone, medium green-colored foliage, and moderately vigorous, mounded growth habit. The male (pollen) parent of the new cultivar is the proprietary *Coreopsis pubescens* breeding selection coded C022-3, not patented, characterized by its single-type, dark yellow-colored inflorescences, medium green-colored foliage, and vigorous, mounded-spreading growth habit. The new cultivar was discovered and selected as a single flowering plant within the progeny of the above stated cross-pollination during October 2013 in a controlled environment in Elburn, Ill.

Asexual reproduction of the new cultivar by terminal stem cuttings since October 2013 in Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Electric Sunshine' as a new and distinct cultivar of *Coreopsis* plant:

1. Single-type, medium yellow-colored inflorescences having a burgundy-red colored eye zone;
2. Medium green-colored foliage; and
3. Vigorous, mounded growth habit.

Plants of the new cultivar differ from plants of the female parent primarily in having a different ray floret color and increased growth vigor. Plants of the new cultivar differ from plants of the male parent primarily in having a different ray floret color, and a less spreading growth habit.

Of the many commercially available *Coreopsis* cultivars, the most similar in comparison to the new cultivar is the *Coreopsis* cultivar UpTick Yellow & Red 'Baluptowed', U.S. Plant Pat. No. 28,865. However, in comparison, plants of the new cultivar differ from plants of 'Baluptowed' in at least the following characteristics:

1. Plants of the new cultivar have fewer ray florets than plants of 'Baluptowed';
2. Plants of the new cultivar are not as cold temperature tolerant as plants of 'Baluptowed'; and
3. Plants of the new cultivar have more growth vigor than plants of 'Baluptowed'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Electric Sunshine'. The plants were approximately four months old. The plants were grown in one-gallon containers for approximately 9 weeks in a greenhouse in Elburn, Ill. followed by 2 weeks in an open-sided polyhouse in West Chicago, Ill. Plants were given two pinches, one at one week before transplant and one two weeks after transplant.

DETAILED BOTANICAL DESCRIPTION

Figure 1:
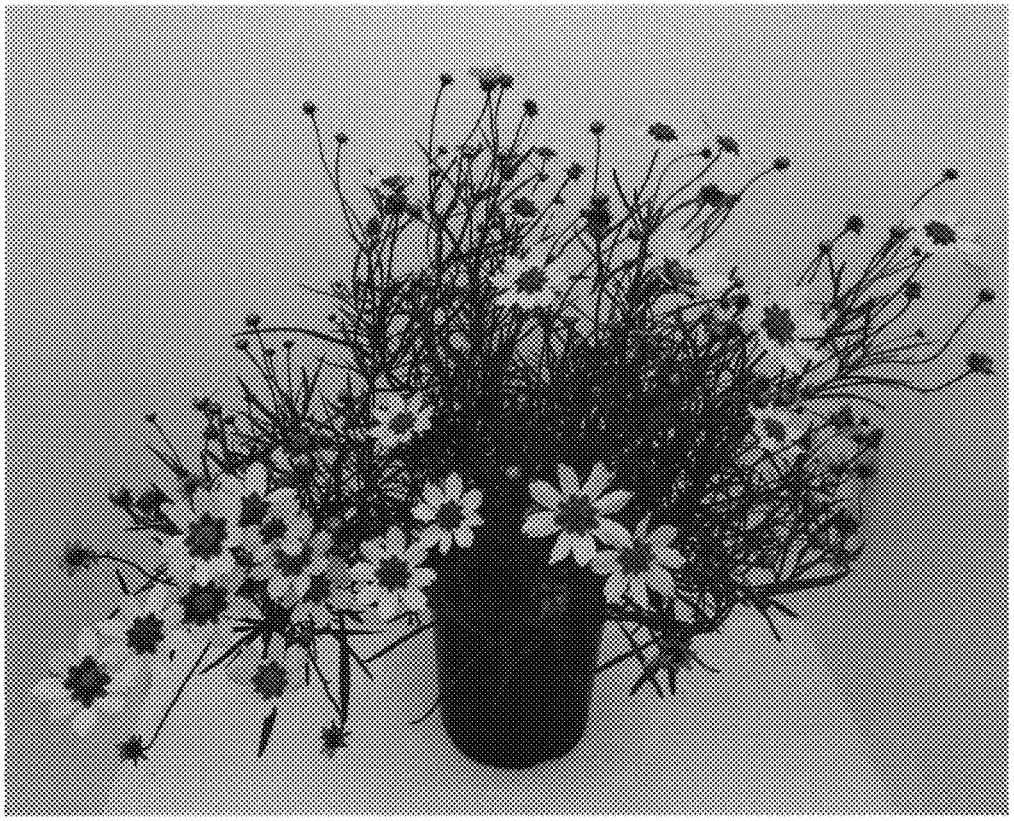
FIG. 1 illustrates a side view of the overall growth and flowering habit of 'Electric Sunshine'.
Figure 2:
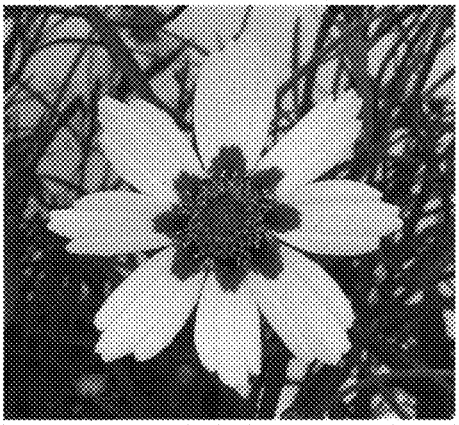
FIG. 2 illustrates a close-up view of an inflorescence of 'Electric Sunshine'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2018 under natural light conditions in West Chicago, Ill.

The following descriptions and measurements describe approximately four-month old plants produced from cuttings from stock plants and grown under conditions comparable to those used in commercial practice. The plants were grown in one-gallon containers for approximately 9 weeks in a greenhouse in Elburn, Ill. followed by 2 weeks in an open-sided polyhouse in West Chicago, Ill. Plants were given two pinches, one at one week before transplant and one two weeks after transplant. Greenhouse temperatures in Elburn, Ill. were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Coreopsis* hybrid 'Electric Sunshine'.

Parentage:

*Female parent*.—Proprietary *Coreopsis rosea* breeding selection coded C025-1, not patented.

*Male parent*.—Proprietary *Coreopsis pubescence* breeding selection coded C022-3, not patented.

Propagation:

*Type cutting*.—Terminal stem.

*Time to initiate roots*.—Approximately 10 to 12 days at 70° F. (21° C.).

*Time to produce a rooted cutting*.—Approximately 5 to 6 weeks at 70° F. (21° C.).

*Root description*.—Fibrous, thin, white to light brown in color.

*Rooting habit*.—Freely branching, dense.

Plant description:

*Commercial crop time*.—Approximately 8 to 10 weeks from a rooted cutting to finish in a one-gallon container.

*Growth habit and general appearance*.—Tender perennial, vigorous, mounded growth habit.

*Hardiness*.—USDA zone 8a (10° F. to 15° F./−12.2° C. to −9.4° C.).

*Size*.—Height from soil level to top of plant plane: Approximately 47.0 cm. Width: Approximately 50.0 cm.

*Branching habit*.—Freely branching, pinching improves basal branching. Quantity of lateral branches per plant: 4 main branches each having approximately 6 lateral branches.

*Lateral branches*.—Strength: Moderately strong. Length to base of peduncle: Approximately 14.0 cm. Diameter: Approximately 3.0 mm to 4.0 mm. Length of central internode: Approximately 6.0 cm. Texture: Glabrous. Color of young and mature stems: 146B.

Foliage description:

*General description*.—Quantity of leaves per main branch: Approximately 6. Type: Simple and trifoliate. Fragrance: None detected. Arrangement: Opposite. Aspect: Acute angle to stem. Shape of leaf and leaflet: Narrowly elliptic. Margin of leaf and leaflet: Entire, ciliate. Apex of leaf and leaflet: Acute. Base of leaf and leaflet: Attenuate, simple leaf sessile. Venation pattern: Pinnate.

*Simple leaf*.—Length: Approximately 6.5 cm. Width: Approximately 6.0 mm. Texture of upper and lower surfaces: Glabrous. Color of upper surface of young and mature foliage: 137A with indistinguishable venation. Color of lower surface of young and mature foliage: Closest to between 138A and 138B with indistinguishable venation.

*Mature trifoliate leaf*.—Length of mature trifoliate leaf: Approximately 10.5 cm. Width of mature trifoliate leaf: Approximately 12.0 cm. Length of terminal leaflet: Approximately 10.3 cm. Width of terminal leaflet: Approximately 7.0 mm. Length of lateral leaflet: Approximately 6.0 cm. Width of lateral leaflet: Approximately 5.0 mm. Texture of upper and lower surfaces: Glabrous. Color of upper surface of young and mature foliage: 137A with indistinguishable venation. Color of lower surface of young and mature foliage: Closest to between 138A and 138B with indistinguishable venation. Length of petiole of mature trifoliate leaf: Approximately 3.0 cm. Diameter of petiole of mature trifoliate leaf: Approximately 2.0 mm. Texture of petiole of mature trifoliate leaf: Sparsely pubescent. Color of upper and lower surfaces of petiole of mature trifoliate leaf: 146B.

Flowering description:

*Flowering habit*.—'Electric Sunshine' is freely flowering under outdoor growing conditions with substantially continuous blooming from spring through late autumn.

*Lastingness of individual inflorescence on the plant*.—Approximately 7 to 10 days.

Inflorescence description:

*General description*.—Type: Daisy-type composite, actinomorphic. Persistent, but doesn't require cleaning to flower. Shape: Round. Aspect: Erect to outwardly facing. Arrangement: Terminal capitulum, positioned above the foliage. Quantity per plant: Approximately 40. Diameter: Approximately 5.7 cm. Depth: Approximately 1.0 cm. Fragrance: Slightly acrid.

*Peduncle*.—Strength: Strong, flexible. Aspect: Erect. Length: Approximately 10.5 cm to 13.0 cm. Diameter: Approximately 1.5 mm. Texture: Glabrous, slightly glossy. Color: 146A.

*Bud*.—Rate of opening: Generally takes 4 to 5 days for bud to progress from first color to fully open inflorescence. Quantity per plant: Approximately 50.

*Bud just before opening*.—Shape: Obovoid. Width: Approximately 7.0 mm. Depth: Approximately 6.0 mm. Color: 163A.

*Ray florets*.—Quantity per inflorescence: Approximately 8. Arrangement: In a single whorl, slightly to non-imbricate. Aspect: Flattened. Shape: Oblong to obovate. Margin: Entire. Apex: Incised. Base: Rounded. Length: Approximately 2.8 cm. Width: Approximately 1.1 cm to 1.3 cm. Texture of upper and lower surfaces: Glabrous, longitudinal ribs. Color of upper surface when first open: 2A with base of 187A and 187B. Color of lower surface when first open: 3B with an underlay of 187B at base. Color of upper surface when fully open: 2B with base of 187A and 187B. Color of lower surface when fully open: 3C with an underlay of 187B at base.

*Disc florets*.—Quantity per inflorescence: Approximately 130. Arrangement: Massed in center of inflorescence. Shape: Tubular. Margin: Entire. Apex: Five acute tips. Base: Fused. Length: Approximately 7.0 mm. Diameter at tube opening: Approximately 2.0 mm. Diameter at base: Approximately 1.0 mm. Texture of outer surface: Glabrous. Texture of inner surface: Glabrous with glandular pubescence on tips. Color of upper or inner surface when first and fully open: Closest to 17C, translucent; tips of 17B. Color of lower or outer surface when fully open: Closest to 17C, translucent; tips of 17B, base of 155D.

*Disc*.—Diameter: Approximately 1.1 cm. Depth: Approximately 5.0 mm.

*Receptacle*.—Shape: Dome. Height: Approximately 1.0 mm. Diameter at base: Approximately 5.0 mm. Color: 145D.

*Phyllaries*.—Quantity per inflorescence Approximately 16. Arrangement: In two equally divided whorls. Base of inner whorl fused into cup-shaped base surrounding receptacle, imbricate, held close to ray florets.

*Outer phyllaries*.—Shape: Lanceolate. Margin: Entire, ciliate. Apex: Acute. Base: Truncate. Length: Approximately 5.0 mm. Width: Approximately 2.0 mm. Texture of upper and lower surfaces: Glabrous, glossy. Color of upper and lower surfaces: 137A with colorless margins.

*Inner phyllaries*.—Shape of free portion: Ovate. Margin: Entire. Apex: Acute. Base: Fused. Length: Approximately 9.0 mm. Width: Approximately 5.0 mm. Texture of upper and lower surfaces: Glabrous. Color of upper and lower surfaces: 163C with cup-shaped portion of closest to 146D.

*Reproductive organs*.—Androecium: Present on disc florets only. Stamen quantity: 5. Stamen length: Approximately 4.0 mm. Filament length: Approximately 1.5 mm. Filament color: 154D. Anther shape: Oblong, basifixed. Anther length: Approximately 2.5 mm. Anther color: 163A. Pollen amount: Abundant. Pollen color: 17A. Gynoecium: Present on disc florets only. Pistil quantity: 1 per floret. Pistil length: Approximately 7.0 mm. Stigma shape: 2-branched. Stigma length: Each branch approximately 1.0 mm. Stigma color: 17B. Style length: Approximately 5.0 mm. Style color: 154D. Ovary length: Approximately 2.0 mm. Ovary color: 155D.

Seed and fruit production: Neither seed nor fruit production has been observed.

Disease and pest resistance: Resistance to pathogens and pests common to *Coreopsis* has not been observed.

What is claimed is:

1. A new and distinct cultivar of *Coreopsis* plant named 'Electric Sunshine', substantially as herein illustrated and described.

* * * * *